United States Patent
Shimoyama et al.

(10) Patent No.: US 6,777,197 B1
(45) Date of Patent: Aug. 17, 2004

(54) METHOD AND TEST KIT FOR MEASURING IMMUNOGLOBULINS REACTIVE WITH AMYLASE AS INDICATION OF CROHN'S DISEASE

(75) Inventors: Takashi Shimoyama, Nishinomiya (JP); Tatsuo Tozawa, Nishinomiya (JP); Masamichi Satomi, Nishinomiya (JP); Yoshihiro Fukuda, Nishinomiya (JP); Ryoki Takahashi, Tokyo (JP); Ritsuko Mochida, Tokyo (JP); Haruhisa Hirata, Tokyo (JP)

(73) Assignee: Wakamoto Pharmaceutical Co., Ltd., Tokyo (JP)

( * ) Notice: Subject to any disclaimer, the term of this patent is extended or adjusted under 35 U.S.C. 154(b) by 18 days.

(21) Appl. No.: 09/604,275

(22) Filed: Jun. 26, 2000

Related U.S. Application Data

(63) Continuation of application No. PCT/JP98/05960, filed on Dec. 25, 1998.

(30) Foreign Application Priority Data

Dec. 26, 1997 (JP) .............................. 9-366837

(51) Int. Cl.[7] ......................... G01N 33/50; G01N 33/53; G01N 33/573
(52) U.S. Cl. ..................... 435/7.92; 435/7.1; 435/7.21; 436/500; 436/506; 424/134.1; 424/143.1; 424/178.1
(58) Field of Search ............................ 424/134.1, 143.1, 424/154.1, 178.1, 185.1, 810, 144.1; 435/2, 4, 5, 6, 7.1, 7.21, 91.2, 240.2, 252.3, 255.1, 320.1; 514/2, 8, 855; 436/64, 500, 506

(56) References Cited

U.S. PATENT DOCUMENTS

| | | | |
|---|---|---|---|
| 4,948,723 A | * | 8/1990 | Hermon-Taylor et al. ...... 435/7 |
| 5,814,457 A | * | 9/1998 | Kern et al. ................... 435/7.1 |
| 6,066,322 A | * | 5/2000 | Levinson ................. 424/144.1 |

OTHER PUBLICATIONS

Troncone et al., "Gut lavage IgG and interleukin 1 receptor antagonist: interleukin 1Beta ration as markers of intestinal inflammation in children with inflammatory bowel disease"., Gut, 1997, vol. 41, p. 60–65.*
Sailer et al., "Serum immunoglobulin levels in ulcerative colitis and Crohn's disease"., Deutsche Medizinische Wochenschrift, 1976, vol. 101., No. 33, pp. 1214–1217.*
Jones et al., "Serum and intestinal fluid immuno globulins and jejunal immun globulin A secretion in Crohn's disease"., 1976, vol. 14, No. 1, pp. 12–19.*
S. Targan et al, *Gastroenterology*, vol. 96 (5), A505 (1989).
S. Bagchi et al, *Clin. Exp. Immunol.*, vol. 55, pp. 41–48 (1984).
K. Das et al, *J. Immunol.*, vol. 150 (6), pp. 2487–2493 (1993).
P. Knoflach et al, *Gastroenterology*, vol. 92, 479–485 (1987).
J. Thoma et al, in *The Enzymes*, 3rd Edition., vol. 5, pp. 115–189; Paul D. Boyer, Editor; Academic Press, New York and London (1971).
Urdal et al., Macroamylase immunoglobulins show high affinity for animal and human amylase., Clinical Chemistry, May 1985, vol. 31, No. 5., pp. 699–702.*
J. Hegnhoj, et al., "Pancreatic function in Crohn's disease", vol. 31, No. 9, pp. 1076–1079, 1990.–Gut.
Richard A. L. Sturdevant, et al., "Azathioprine–Related Pancreatitis in Patients with Crohn's Disease", GASTROENTEROLOGY, vol. 77, pp. 883–886, 1979.

* cited by examiner

*Primary Examiner*—Long V. Le
*Assistant Examiner*—Lisa V Cook
(74) *Attorney, Agent, or Firm*—Oblon, Spivak, McClelland, Maier & Neustadt, P.C.

(57) ABSTRACT

A method for diagnosing Crohn's disease by detecting the presence of immunoglobulins, reactive with an amylase, in a specimen by an immunologic or enzymologic method using the amylase, and a test kit for this method.

11 Claims, 2 Drawing Sheets

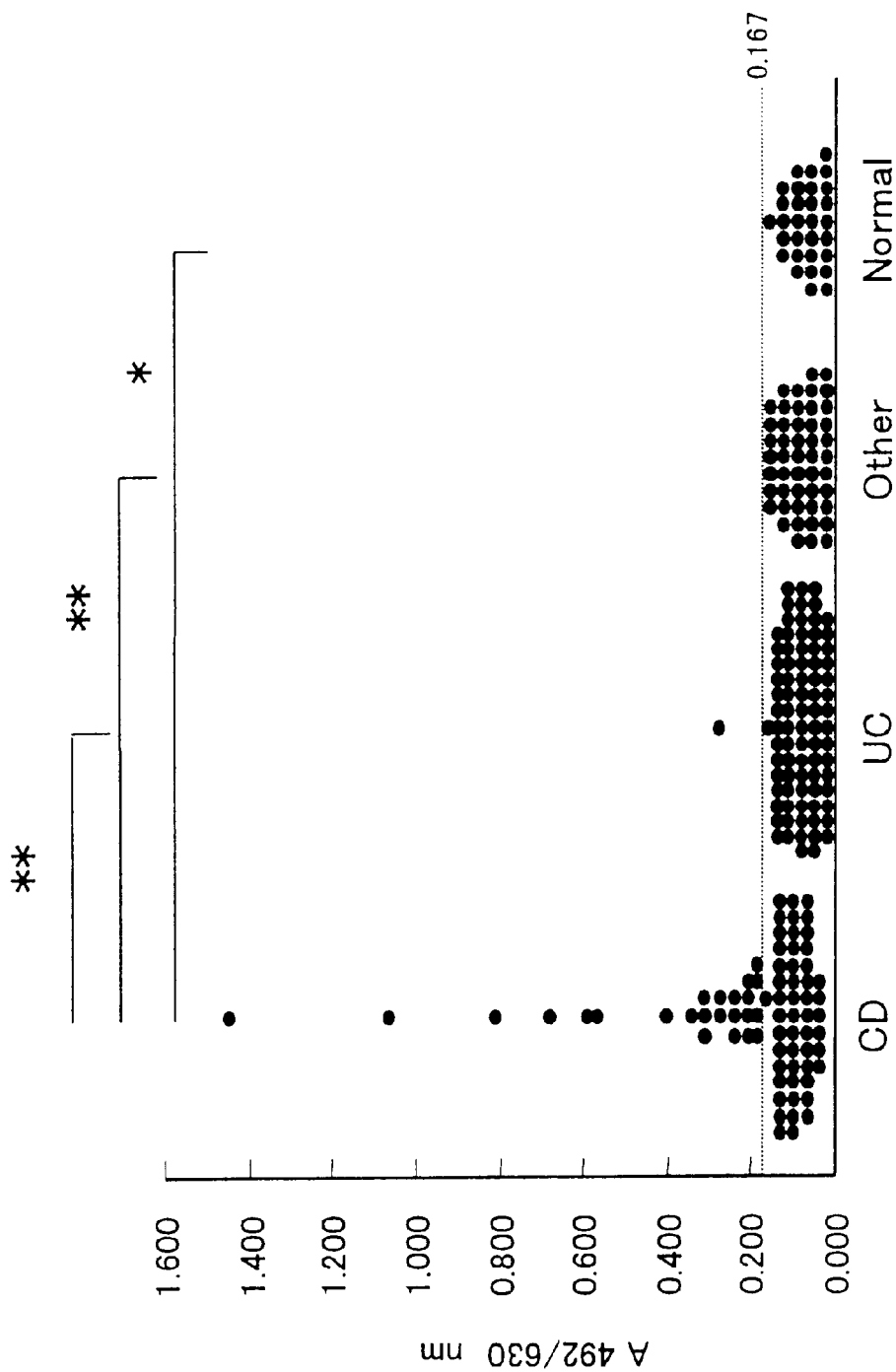
FIG. 1 Reactivity with porcine amylase

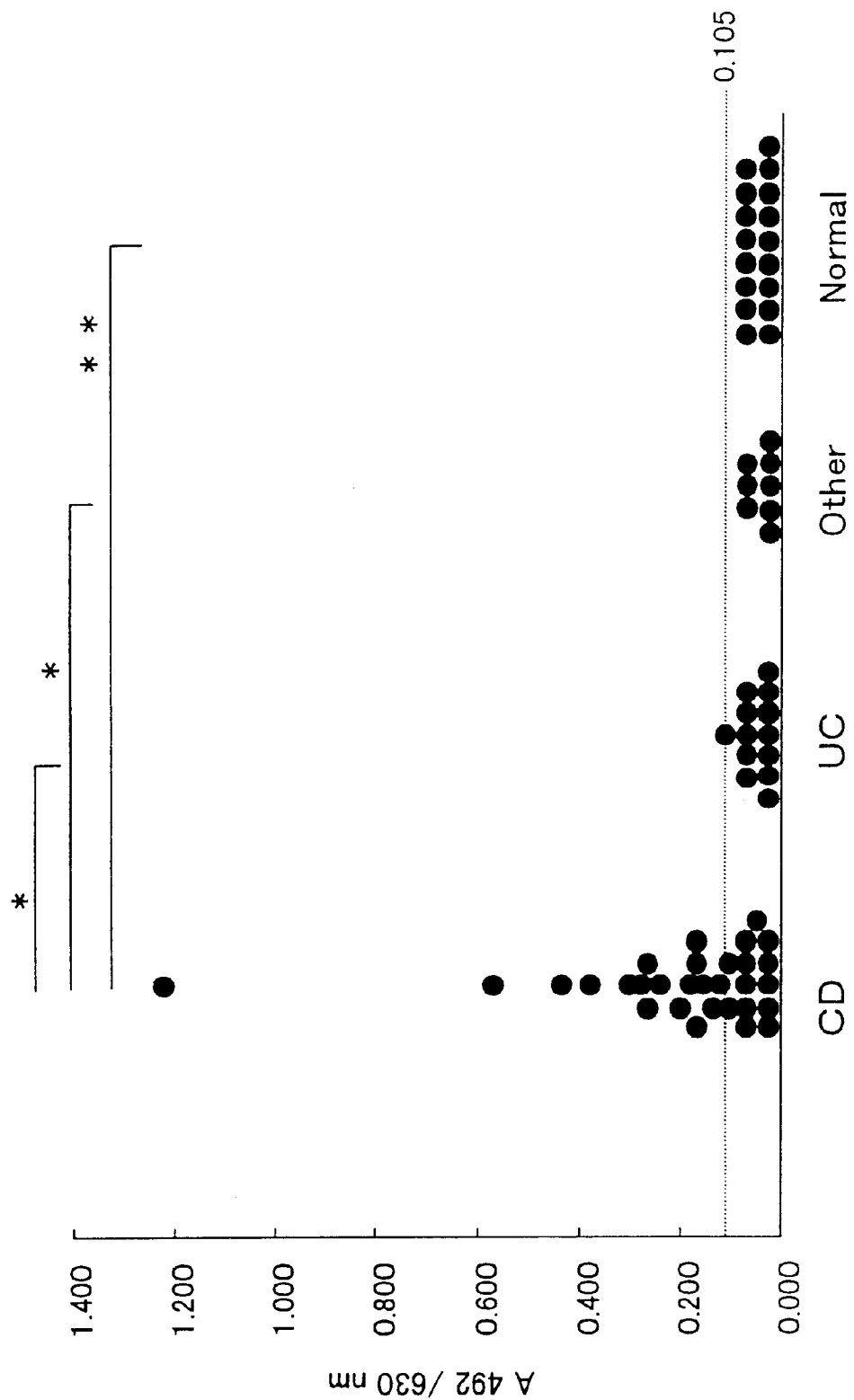
FIG. 2 Reactivity with bovine amylase

METHOD AND TEST KIT FOR MEASURING IMMUNOGLOBULINS REACTIVE WITH AMYLASE AS INDICATION OF CROHN'S DISEASE

This application is a Continuation of International Application No. PCT/JP98/05960, filed Dec. 25, 1998. It also claims priority to JAPAN 9-366837, filed Dec. 26, 1997.

TECHNICAL FIELD

The present invention relates to a method and a test kit for diagnosing Crohn's disease. In particular, the invention relates to a method for easily and rapidly diagnosing Crohn's disease by an immunologic or enzymologic method used in the field of clinical examinations.

PRIOR ART

In inflammatory intestinal diseases, Crohn's disease and ulcerative colitis are classified into a group of cryptogenic and idiopathic inflammatory intestinal diseases and they are designated as intractable diseases by the Ministry of Health and Welfare. These diseases are diagnosed based on the diagnostic standards prepared by the group of researchers who conducted the investigation and research on intractable inflammatory intestinal diseases specified by the Ministry of Health and Welfare. More specifically, after excluding infectious enteritis by the stool culture or the like, the disease is diagnosed by a combination of the clinical findings and the results of gastrointestinal contrast-radiography, endoscopy and histological examinations. However, in some cases, the diagnosis is still difficult to make even by these methods. Particularly, it is difficult to distinguish Crohn's disease from ulcerative colitis in many cases. In addition, skillful doctors are needed to conduct the gastrointestinal contrast-radiography and endoscopy examinations and these examinations usually cause the patients physical and mental pains. Under these circumstances, there is a worldwide demand for the development of a specific, accurate clinical examination method capable of easily and rapidly diagnosing Crohn's disease and ulcerative colitis.

It was reported that blood serums of patients with Crohn's disease contain antineutrophilic leukocyte antibodies (Targan, S., et al.: Gastroenterology, 96, A 505, 1989) and anti-small intestine antibodies (Bagchi, S., et al.: Clin. Exp. Immunol., 55, 44–48, 1984), while those of patients with ulcerative colitis contain antitropomyosin antibodies (Das, K. n., et al.: J. Immunol., 150, 2487–2493, 1993), anticasein antibodies (Knoflach, P., et al.: Gastroenterology, 92, 479–485, 1987) or antimucin antibodies. Although some of those antibodies were reported to be specific to the above respective diseases, no antibody examination has yet been employed in the diagnosis of these diseases for the following reasons: Although the antibodies were reported to be specific to Crohn's disease or ulcerative colitis, the data on these diseases was insufficient so that accurate clinical examinations could not be conducted. For example, the number of the cases was too small (small intestine protein, tropomyosin and mucin) or they had no specificity (neotrophilic leukocyte and casein). From this viewpoint, it can be said that the development of an accurate clinical examination method capable of easily and rapidly diagnosing Crohn's disease and ulcerative colitis by examining the specific serum antibodies is very important in the clinical field.

DISCLOSURE OF THE INVENTION

The object of the present invention is to provide an accurate clinical examination method capable of easily and rapidly diagnosing Crohn's disease and ulcerative colitis in mammals, particularly human beings, and a test kit used for the method.

The present invention relates to (1) a method for diagnosing Crohn's disease, which comprises detecting the presence of an immunoglobulin or immunoglobulins, reactive with an amylase, in a specimen.

The present invention also relates to (2) a method for diagnosing Crohn's disease, which comprises detecting the presence of immunoglobulins, reactive with an amylase, in a specimen by an immunologic or enzymologic method.

Further, the present invention relates to (3) a method for diagnosing Crohn's disease, which comprises detecting the presence of immunoglobulins, reactive with an amylase, in a specimen by an immunologic method comprising reacting immunoglobulins, reactive with the amylase, in a specimen with the amylase immobilized on a support, reacting the product with a labeled product of a substance reactive with the immunoglobulins that are reactive with the amylase and determining an amount of the labeled reaction product.

The present invention relates to (4) a method for diagnosing Crohn's disease, which comprises detecting the presence of immunoglobulins, reactive with an amylase, in a specimen by the enzymologic method comprising reacting immunoglobulins, reactive with the amylase, in a specimen with the amylase and then determining the amylase activity of the reaction product.

The present invention relates to (5) a method for diagnosing Crohn's disease according to the above methods, wherein the amylase is porcine amylase or bovine amylase.

The present invention relates to (6) a test kit for diagnosing Crohn's disease by detecting the presence of immunoglobulins, reactive with an amylase, in a specimen, the kit comprising the amylase and a reagent for determining the amylase activity or a reagent for determining the marker enzyme activity.

The present invention relates to (7) a test kit for diagnosing Crohn's disease by detecting the presence of immunoglobulins, reactive with amylase, in a specimen, by the immunologic method, the kit comprising a support on which the amylase is immobilized; an enzyme-labeled substance selected from the group consisting of an enzyme-labeled anti-human IgG antibody, an enzyme-labeled anti-human IgA antibody, an enzyme-labeled protein A, an enzyme-labeled protein G and an enzyme-labeled Jacalin; and an enzyme activity-determining reagent.

The present invention relates to (8) a test kit for diagnosing Crohn's disease according to the above test kit, wherein the amylase is porcine amylase or bovine amylase.

BRIEF DESCRIPTION OF THE DRAWINGS

FIG. 1 is a scatter diagram showing the results of the detection by enzyme immunoassay of the presence of immunoglobulins reactive with porcine amylase in the serums of patients having Crohn's disease (CD; 75 cases), ulcerative colitis (UC; 84 cases), or other diseases such as gastric ulcer or duodenal ulcer and macroamylasemia (Others, 48 cases) and the serums of healthy controls (Normal; 30 cases). Symbols "*" and "**" represent the statistical significant differences (*: $p<0.05$, **: $p<0.01$) between the results for the patients having Crohn's disease, those for patients with ulcerative colitis, those for patients with other diseases such as gastric ulcer or duodenal ulcer and macroamylasemia and those for healthy controls. The value 0.167 is the cutoff value determined from the results of the determination of the serums of the healthy controls.

FIG. 2 is a scatter diagram showing the results of the detection by enzyme immunoassay of the presence of immunoglobulins reactive with bovine amylase in the serums of patients having Crohn's disease (CD; 30 cases), ulcerative colitis (UC; 13 cases), or other diseases such as gastric ulcer or duodenal ulcer and macroamylasemia (Others, 8 cases) and the serums of healthy controls (Normal; 18 cases). Symbols "*" and "**" represent the statistical significant differences (*: $p<0.05$, **: $p<0.01$) between the results for the patients having Crohn's disease, those for patients with ulcerative colitis, those for patients with other diseases such as gastric ulcer or duodenal ulcer and macroamylasemia and those for healthy controls. The value 0.105 is the cutoff value determined from the results of the determination of the serums of the healthy controls.

BEST MODE FOR CARRYING OUT THE INVENTION

After conducting intensive epidemiological, immunological and biochemical investigations for the purpose of developing an ideal examination method for diagnosing Crohn's disease in mammals, particularly human beings, the inventors have found that the blood of patients having Crohn's disease contains a significantly large amount of immunoglobulins reactive with an amylase. The present invention has been completed on the basis of this finding.

Namely, the present invention provides a method for diagnosing Crohn's disease, wherein the presence of immunoglobulins, reactive with an amylase, in a specimen is detected by the amylase.

For the detection of the presence of immunoglobulins reactive with the amylase, either an immunological determination method, such as enzyme immunoassay, or an enzymologic determination method can be employed.

The amylases usable in the present invention are heterologous amylases. In the examination method for diagnosing Crohn's disease in human beings, any amylase other than that from human beings is usable. Preferred amylases are those derived from farm animals such as pigs, cows, chickens and horses. Among these, amylases derived from pigs and cows are particularly suitable for use. Although the present invention will be described below with reference to the examination method for diagnosing Crohn's disease in human beings, the invention is not limited to this method.

Although most of the human body fluids are usable as the samples in the method of the present invention, whole blood, serum, plasma, urine, saliva and the like are preferred. The serums or plasmas of patients are particularly preferred.

Although the immunological determination methods are not particularly limited, enzyme immunoassay, immunochromatography, and the like are preferred. In all these methods, the immunoglobulins, reactive with the amylase, in a specimen is reacted with the amylase immobilized on a support, the reaction product is reacted with a labeled product of a substance that is reactive with said immunoglobulins, reactive with the amylase and the amount of the labeled reaction product is determined. In enzyme immunoassay, the amount of the labeled reaction product is determined in accordance with the activity of the enzyme using the enzyme-labeled substance. In immunochromatography, the amount of the labeled reaction product is determined in accordance with the amount of colored product using a labeled product composed of color particles.

Enzyme immunoassay is preferably employed in the present invention, which assay method is capable of easily obtaining numerical values of the amount of the labeled reaction product, i.e. the amount of the immunoglobulins reactive with the amylase, in the specimen. In a preferred enzyme immunoassay, the immunoglobulins reactive with an amylase in the specimen is reacted with an amylase immobilized on a support, the reaction product is reacted with a substance, that is reactive with the immunoglobulins reactive with the amylase, preferably with an enzyme-labeled product of an anti-human immunoglobulin antibody, protein A, protein G or Jacalin; and the amount of the labeled reaction product is determined on the basis of the enzymatic activity. Suitable supports are, for example, plastics such as polystyrene resins, polycarbonate resins, silicone resins and nylon, and glass. The amylase may be immobilized on the support by the physical adsorption or chemical bonding. Suitable enzymes for the labeling are peroxidases, β- galactosidases and alkaline phosphatases.

On the other hand, enzymologic determination includes a method in which the principle for determination of the amount of immunoglobulins is the fact that the immunoglobulins reactive with the amylase in the specimen inhibits the amylase activity. The easiest method for determining the degree of inhibition of the amylase activity is an in vitro reaction method. In this method, an amylase solution of a known concentration is mixed with the specimen in a ration of 1:1 in a test tube, and after leaving the mixture as is for a predetermined period of time, the amylase activity of the mixture is determined by a known method for determining this activity [Thoma, J. A., et al: The Enzyme ($3^{rd}$ ed.), 5, 115–189, 1971]. Although the activity determination method is not particularly limited, a kit for determining amylase in the blood, which contains a synthetic substrate such as 4-nitrophenyl-maltoheptaoside, or p-nitrophenylbenzyl-α-maltopentaoside, is preferred. The degree of the inhibition of the amylase activity was calculated by deducting the separately determined amylase activity of the specimen diluted to ½ concentration and also deducting that of the amylase solution diluted to ½ concentration from the amylase activity of the liquid mixture, respectively.

Further, human amylase activity which is not inhibited by the immunoglobulins reactive with the amylase is recognized in the blood. Therefore, another preferred method of the present invention may comprise the steps of reacting the immunoglobulins reactive with the amylase, in the specimen, with the amylase, separating the human amylase using a carrier for the separation of the serum protein, and determining the degree of inhibition of the amylase activity in the reaction product. Suitable carriers for separating the serum protein are, for example, cellulose acetate membrane, agarose gel, polyacrylamide gel, dextran gel and the like. The separation methods using the carrier are, for example, electrophoresis, liquid chromatography and the like. In the present invention, electrophoresis is recommended in view of its easiness and rapidness.

The present invention further provides a test kit for diagnosing Crohn's disease by detecting the presence of immunoglobulins, reactive with an amylase, in a specimen, which kit contains the amylase and a reagent for determining the amylase activity or a reagent for determining the marker enzyme activity.

When enzyme immunoassay is employed as the immunological determination method, the test kit of the present invention contains a support on which an amylase is immobilized; an enzyme-labeled substance selected from the group consisting of an enzyme-labeled anti-human IgG antibody, an enzyme-labeled anti-human IgA antibody, an enzyme-labeled protein A, an enzyme-labeled protein G and an enzyme-labeled Jacalin; and a marker enzyme activity-determining reagent.

When the in vitro reaction method is employed as the enzymologic determination method, the test kit of the present invention contains an amylase and a reagent for determining the amylase activity.

When electrophoresis is employed as the enzymologic determination method, the test kit of the present invention contains a cellulose acetate membrane which is the carrier for separating the serum protein, in addition to an amylase and Blue Starch which is a reagent for determining the amylase activity.

The test kit of the present invention for diagnosing Crohn's disease can further contain a buffer, a standard serum, etc.

The following Examples will further illustrate the present invention, which Examples by no means limit the invention.

EXAMPLES

Example 1

Detection by Enzyme Immunoassay of the Presence of Immunoglobulins Reactive with Porcine Amylase in the Blood 1) Preparation of Support Immobilizing Porcine-amylase 0.2 ml of porcine pancreatic amylase (A6225; a product of Sigma) diluted to a concentration of 10 $\mu$g/ml with phosphate-buffered saline (PBS) was fed into each well of a 96-well microtiter plate (a product of Costar). After a reaction was conducted at 4° C. overnight, the liquid was removed from each well, then 0.25 ml of PBS was added to each well to wash it, and the liquid was removed. This washing operation was repeated three times. 0.25 ml of PBS containing 0.1% of skim milk was fed into each well as the masking reagent, and the incubation was conducted at 37° C. for one hour. After the completion of the masking, the liquid was removed from each well, and as a preservative, 0.25 ml of PBS containing 0.1% of NaN$_3$ and 0.1% of skim milk was fed into each well. The support thus prepared was kept at 4° C.

2) Detection of the Presence of Immunoglobulins, Reactive with Porcine Amylase, in Blood A sandwich method was employed for the detection of the presence of immunoglobulins, reactive with porcine amylase, in human blood. In this method, the preservative was removed from the microtiter plate, on which porcine amylase was solid-phased, as described above. 0.2 ml of the serum or plasma to be examined, which had previously been diluted to a concentration of 1/80 with PBS containing 0.05% of skim milk, was fed into each well. After stirring with a mixer used for microtiter plate for about one minute, the reaction was conducted at 37° C. for one hour. After removing the liquid from each well, each well was washed with 0.25 ml of PBS containing 0.05% of Tween 20 three times. Then, peroxidase-labeled anti-human IgG antibody was diluted to a suitable concentration and 0.2 ml thereof was fed into each well. After the reaction was carried out again at 37° C. for one hour, the liquid was removed, and each well was again washed. After the liquid was completely removed from each well, 0.2 ml of a substrate solution (1.5 mg/ml aqueous o-phenylenediamine solution containing 0.01% of hydrogen peroxide) was added thereto, and the reaction was conducted at room temperature for 10 minutes. Then 0.05 ml of 3.5 N sulfuric acid was fed into each well to terminate the reaction. After the termination of the reaction, the absorbance (absorbance at 492 nm—absorbance at 630 nm) of the plate was determined with a colorimeter for a microtiter plate (a product of Bio-Rad).

3) Confirmation of Reactivity

By using two serum samples of patients having Crohn's disease and one serum sample of a healthy control, the dilution ratio of the serum was varied in the range of 1/40 to 1/1280, then the reactivity of the diluted serums were determined. The results are shown in Table 1. It was recognized that as the serums of the patients having Crohn's disease were diluted, the absorbance was lowered. No remarkable lowering of the absorbance was observed in the serum of the healthy control when it was diluted to a concentration of 1/80 or less. Based on these results, the dilution ratio of the serum in the determination was fixed at 1/80.

TABLE 1

Confirmation of reactivity

| Dilution ratio of serum | Crohn's disease patient 1 | Crohn's disease patient 2 | Healthy control |
| --- | --- | --- | --- |
| 40 | 0.834 | 0.630 | 0.187 |
| 80 | 0.811 | 0.525 | 0.109 |
| 160 | 0.430 | 0.416 | 0.092 |
| 320 | 0.245 | 0.256 | 0.064 |
| 640 | 0.135 | 0.167 | 0.070 |
| 1280 | 0.081 | 0.093 | 0.070 |

4) Confirmation of Reproducibility

The simultaneous reproducibility and inter-day reproducibility of each of the serum samples of patients having Crohn's disease and that of the healthy control were confirmed. The simultaneous reproducibilities of them are shown in Table 2. The coefficient of variation was 1.7 to 3.3%. The inter-day reproducibilities are shown in Table 3. The coefficient of variation was 1.8 to 3.8%.

In all the examinations, a sufficient reproducibility was obtained. A significant difference was observed between the absorbance of the patients having Crohn's disease and that of the healthy control (significance level: 1%).

TABLE 2

Simultaneous reproducibility

| n | Crohn's disease patients | Healthy controls |
| --- | --- | --- |
| 1 | 0.608 | 0.118 |
| 2 | 0.596 | 0.120 |
| 3 | 0.600 | 0.122 |
| 4 | 0.602 | 0.114 |
| 5 | 0.616 | 0.123 |
| 6 | 0.599 | 0.122 |
| 7 | 0.586 | 0.120 |
| 8 | 0.598 | 0.118 |
| 9 | 0.606 | 0.129 |
| 10 | 0.623 | 0.120 |
| Average | 0.603 | 0.121 |
| Standard deviation | 0.010 | 0.004 |
| Coefficient of variation | 1.7(%) | 3.3(%) |

TABLE 3

| | Inter-day reproducibility | |
|---|---|---|
| n | Crohn's disease patients | Healthy controls |
| 1 | 0.608 | 0.129 |
| 2 | 0.616 | 0.121 |
| 3 | 0.598 | 0.130 |
| 4 | 0.600 | 0.127 |
| 5 | 0.584 | 0.135 |
| 6 | 0.608 | 0.133 |
| Average | 0.602 | 0.129 |
| Standard deviation | 0.011 | 0.005 |
| Coefficient of variation | 1.8(%) | 3.8(%) |

Example 2

Comparison with Ulcerative Colitis and Other Diseases

The presence of immunoglobulins, reactive with porcine amylase, in the serums of patients having Crohn's disease (75 cases), ulcerative colitis (84 cases), or other diseases such as gastric ulcer or duodenal ulcer and macroamylasemia (48 cases) and the serums of healthy controls (30 cases) was detected by using the same method as that used in Example 1. The results are shown in the scatter diagram (FIG. 1). In FIG. 1, each point represents an average of the three determination results. On the basis of these results, the significant difference between the amount of immunoglobulins in the serums in the Crohn's disease cases and each of those in the serums in the cases of ulcerative colitis, other diseases or healthy controls, were respectively examined. In all the cases, the amount of immunoglobulins, reactive with porcine amylase, in the serums in the Crohn's disease cases was significantly larger than those of other diseases. The number of positive cases of immunoglobulins reactive with porcine amylase were compared with each other on the basis of the cutoff value (0.167, average+2×standard deviation) determined from the average (0.105) of the serums of healthy controls and the standard deviation (0.031). The results were: 23 cases for Crohn's disease and one case for, ulcerative colitis. These results indicate that this determination method can be employed for the differential diagnosis of Crohn's disease.

Example 3

Detection of Immunoglobulins, Reactive with Porcine Amylase, in Blood by Enzymologic Determination Method (In Vitro Reaction Method)

100 µl of a serum sample was mixed with 100 µl of a porcine pancreatic amylase (about 1,000 to 2,000 units), and the obtained mixture was allowed to stand at room temperature for a period of 2 hours to one night. Then the amylase activity of the liquid mixture was determined with an amylase determination kit (L-type Wako Amylase; a product of Wako Pure Chemical Industries, Ltd.) containing p-nitrophenylbenzyl-α-maltopentaoside as the substrate and an automatic analyzer (Hitachi 7350). Further, the serum sample and porcine pancreatic amylase were each diluted to a concentration of ½ with saline and their amylase activities were determined. The rate of amylase activity inhibition was calculated according to the formula: (activity of the liquid mixture)−(activity of the serum sample diluted to ½ concentration)−(activity of porcine pancreatic amylase solution diluted to ½ concentration). The result of the calculation was shown as an inactivation activity. The serums of patients having Crohn's disease (86 cases), ulcerative colitis (86 cases), or other diseases such as gastrointestinal diseases and liver diseases and healthy controls (25 cases) were examined by this method. As a result, it was found that the activities to inactivate the amylase of the serums of the healthy controls were in the range of 0 to −30 units/l. When the cutoff value was determined to be −30 units/l, the number of cases of positive inactivation activity was 29 in the serums in the Crohn's disease cases, while this number was only 1 in the serums in the ulcerative colitis cases or 0 in the serums in the cases of other diseases and healthy controls. It was thus proved that the presence of immunoglobulins, reactive with porcine amylase, in the blood can be detected also by this method and that the method can be employed for the differential diagnosis of Crohn's disease.

Example 4

Detection of Immunoglobulins, Reactive with Porcine Amylase, in Blood by Enzymologic Determination Method (Electrophoresis)

1) Electrophoresis with Cellulose Acetate Membrane

About 600 units/ml of porcine pancreatic amylase was added to a serum sample or saline (control). 0.3 µl of the serum sample or saline thus prepared was applied to a cellulose acetate membrane (trade name: Titan; a product of Helena Research Institute) equilibrated with a 0.26 M tris borate buffer (pH 9.1) with an applicator. As the buffers for the migration, 0.26 M tris borate buffer solution (pH 9.1) was used on the cathode side and Veronal buffer solution (pH 8.6) was used on the anode side. The migration was conducted at 120 V for 2 hours.

2) Determination of Inhibition of Amylase Activity 0.8 g of Blue Starch (neoamylase test "Dai-ichi"; a product of Dai-ichi Kagaku Yakuhin Co.) was dissolved in 5.5 ml of water to obtain a substrate solution. The cellulose acetate membrane used for the migration was placed on a tray. 5.5 ml of Blue Starch was uniformly placed on the membrane. After covering the tray with another tray, the incubation was conducted at 37° C. for 40 to 50 minutes. After the completion of the reaction, Blue starch was washed off from the membrane with methanol. The cellulose acetate membrane was placed into methanol, and they were allowed to stand for 10 minutes. The porcine amylase inhibition activity was judged by observing how deep was the blue color of the blue band formed by the decomposition of Blue Starch and the change of the electrophoresis pattern. The results of the examinations wherein the serums described in Example 3 were used were as follows. Liquids obtained by adding porcine amylase to the serums of patients having Crohn's disease, which serums exhibited positive inactivation activity, exhibited activity bands having a porcine amylase activity lower than that of the control and also a migration pattern similar to an abnormal migration pattern such as the tailing characteristic of human macroamylasemia. On the other hand, when the porcine amylase was added to the serums of the patients with ulcerative colitis or those of the healthy controls, the porcine amylase activity bands were similar to that of the control. It was thus proved that the presence of the immunoglobulins, reactive with porcine amylase, in the blood can be detected by this method.

Example 5

Detection of Immunoglobulins, Reactive with Bovine Amylase, in Blood by Enzyme Immunoassay 1) Purification of Bovine Amylase The bovine amylase was purified as follows. In the course of the process, the temperature was kept at 4° C. or lower.

40 ml of 0.1 M Tris-HCl buffer (pH 7.2) [Buffer A] containing 5 mM of $CaCl_2$ and 50 mM of NaCl was added to 2 g of a bovine pancreas acetone powder (Pancreas acetone powder, Bovine: a product of Sigma), and the obtained mixture was stirred for 15 minutes. After centrifugation (11,400×g) for 10 minutes, supernatant liquid was recovered. Ammonium sulfate was then added to the supernatant liquid to realize 65% saturation. After centrifugation (25,600×g) for 15 minutes, the obtained precipitates were dissolved in 30 ml of 20% saturated ammonium sulfate dissolved in buffer A. The insoluble matter was removed by centrifugation, and the obtained product was loaded in Butyl-Toyopearl 650C column (2.1×7.3 cm) (a product of Tosoh Corporation) previously equilibrated with buffer A containing 20% saturated ammonium sulfate solution. The column was then washed with the buffer A containing 20% saturated ammonium sulfate solution. After elution with buffer A containing 10% saturated ammonium sulfate solution and then with buffer A, the fraction having the amylase activity was recovered, to which fraction ammonium sulfate was added to realize 60% saturation. The precipitate obtained after centrifugation (25,600×g) for 15 minutes was obtained in the form of the purified bovine amylase (enzyme activity: 130 units, amount of protein: 3.98 mg).

2) Preparation of Support on which Bovine Amylase is Immobilized, and Determination Using the Same 0.2 ml of the purified bovine pancreatic amylase diluted to a concentration of 10 μg/ml with phosphate-buffered saline (PBS) was fed into each well of a 96-well microtiter plate (a product of Costar). After a reaction conducted at 4° C. overnight, a microtiter plate, on which bovine amylase was solid-phased, was prepared in the same manner as that in Example 1. In the determination, human serum was used as the sample.

3) Confirmation of Reactivity

The reactivity was confirmed by using 3 serum samples of patients having Crohn's disease and 3 serum samples of healthy controls. The serum dilution rate was 1/80. The results of the confirmation of the reactivity are shown in Table 4. The values of the serums of the patients having Crohn's disease were higher than those of the healthy controls.

TABLE 4

Results of detection of presence of immunoglobulins, reactive with bovine amylase, in serum:

| No. | Serums of patients of Crohn's disease | Serums of healthy controls |
| --- | --- | --- |
| 1 | 0.571 | 0.027 |
| 2 | 0.279 | 0.082 |
| 3 | 1.220 | 0.067 |

4) Comparison with Ulcerative Colitis and Other Diseases

The serums of patients having Crohn's disease (30 cases), ulcerative colitis (13 cases), and other diseases such as gastric ulcer, duodenal ulcer and macroamylasemia (8 cases) and the serums of healthy controls (18 cases) were determined in the same manner as that in Example 5. The results are shown in the scatter diagram (FIG. 2). From the results thus obtained, significant differences between the patients having Crohn's disease and those with ulcerative colitis and other diseases as well as healthy controls were determined. In all the cases, the amount of immunoglobulins, reactive with bovine amylase, in the serums of the Crohn's disease cases was significantly higher. The number of positive cases of immunoglobulins reactive with bovine amylase was determined on the basis of the cutoff value (0.104, average+ 2×standard deviation) determined from the average (0.052) of the serums of healthy controls and the standard deviation (0.026). Nineteen (19) positive cases were found in only Crohn's disease cases while no positive case was found in the other diseases. These results indicate that the detection of the presence of immunoglobulins, reactive with bovine amylase, in the serum is useful for the differential diagnosis of Crohn's disease.

Industrial Applicability

The present invention provides a method and a test kit for diagnosing Crohn's disease, characterized by detection of the presence of immunoglobulins, reactive with amylase, in blood by an immunologic or enzymologic method using amylase. As shown in Examples, the easy and rapid diagnosis of Crohn's disease, particularly, the differential diagnosis of ulcerative colitis, is made possible by the examination method and using the test kit of the present invention.

What is claimed is:

1. A method for diagnosing Crohn's disease comprising:
   (1) contacting a sample from a subject to be tested for the presence of Crohn's disease with amylase for a time and under conditions suitable for specific binding between the amylase and an immunoglobulin which can be specifically bound to the amylase that may be contained within the sample, and
   (2) detecting the amount of immunoglobulin specifically bound to the amylase, wherein the presence of immunoglobulin specifically binding to amylase is indicative of Crohn's disease.

2. The method of claim 1, further comprising:
   comparing the amount of an immunoglobulin which can be specifically bound to the amylase in a sample obtained from a patient tested for the presence of Crohn's disease with the amount of an immunoglobulin which can be specifically bound to the amylase present in a sample obtained from one or more healthy subject (s), wherein an elevated amount of an immunoglobulin which can be specifically bound to the amylase compared to the level of an immunoglobulin which can be specifically bound to the amylase present in said healthy subject(s) is indicative of Crohn's disease.

3. The method of claim 1, wherein the detection step (2) is conducted by an immunologic determination method.

4. The method of claim 3, wherein said method comprises:
   (i) contacting a labeled product of a substance which binds to said immunoglobulins with said immunoglobulin bound to the amylase obtained in step (1), to obtain labeled product bound to said immunoglobulin bound to said amylase;
   (ii) removing unbound labeled product;
   (iii) detecting the amount of said labeled product bound to said immunoglobulin bound to said amylase; and
   (iv) correlating (a') said amount of said labeled product bound to said immunoglobulin bound to said amylase with (b') the amount of immunoglobulin which binds to said amylase, to determine the amount of immunoglobulin which binds to said amylase in the sample.

5. The method of claim 1, wherein said amylase is porcine amylase.

6. The method of claim 1, wherein said amylast is bovine amylase.

7. A method for diagnosing Crohn's disease comprising:
   (1) contacting a sample from a subject to be tested for the presence of Crohn's disease with a known concentration of amylase for a time and under conditions suitable for specific binding between the amylase and an immunoglobulin which can be specifically bound to the amylase that may be contained within the sample, and
   (2) detecting the amount of unbound amylase, deducing the detected amount of unbound amylase from the known concentration of amylase to determine the amount of immunoglobulin specifically bound to the amylase, wherein the presence or immunoglobulin specifically binding to amylase is indicative of Crohn's disease.

8. The method of claim 7, wherein detection step (2) is conducted by an enzymologic determination method.

9. The method of claim 8, wherein said method comprises:
   (i) detecting the unbound amylase activity in the product obtained in step (1); and
   (ii) correlating (a') said unbound amylase activity with (b') the amount of an immunoglobulin which binds to said amylase, to determine the amount of an immunoglobulin which binds to said amylase in the sample.

10. The method of claim 7, wherein said amylase is porcine amylase.

11. The method of claim 7, wherein said amylast is bovine amylase.

* * * * *